United States Patent
Trofimov et al.

(10) Patent No.: US 7,174,198 B2
(45) Date of Patent: Feb. 6, 2007

(54) NON-INVASIVE DETECTION OF ANALYTES IN A COMPLEX MATRIX

(76) Inventors: Igor Trofimov, 16 Camp Washington Rd., Long Valley, NJ (US) 07853; Stephen A. Lyon, 16 Tunager La., Cranbury, NJ (US) 08512

(*) Notice: Subject to any disclaimer, the term of this patent is extended or adjusted under 35 U.S.C. 154(b) by 254 days.

(21) Appl. No.: 10/745,092

(22) Filed: Dec. 23, 2003

(65) Prior Publication Data

US 2004/0135085 A1 Jul. 15, 2004

Related U.S. Application Data

(60) Provisional application No. 60/436,761, filed on Dec. 27, 2002.

(51) Int. Cl.
*A61B 5/00* (2006.01)
(52) U.S. Cl. ............................ 600/322; 600/316
(58) Field of Classification Search ........ 600/309–310, 600/316, 322, 336; 356/39–40
See application file for complete search history.

(56) References Cited

U.S. PATENT DOCUMENTS

| | | | | |
|---|---|---|---|---|
| 3,983,507 | A * | 9/1976 | Tang et al. | ............... 372/105 |
| 4,200,808 | A * | 4/1980 | Herbst | ............... 359/329 |
| 4,225,233 | A * | 9/1980 | Ogan | ............... 356/308 |
| 4,349,907 | A * | 9/1982 | Campillo et al. | ............... 372/102 |
| 4,655,225 | A | 4/1987 | Dahne et al. | |
| 4,975,581 | A | 12/1990 | Robinson et al. | |
| 5,028,787 | A | 7/1991 | Rosenthal et al. | |
| 5,070,874 | A | 12/1991 | Barnes et al. | |
| 5,086,229 | A | 2/1992 | Rosenthal et al. | |
| 5,137,023 | A | 8/1992 | Mendelson et al. | |
| 5,144,630 | A * | 9/1992 | Lin | ............... 372/22 |
| 5,267,152 | A | 11/1993 | Yang et al. | |
| 5,348,003 | A * | 9/1994 | Caro | ............... 600/310 |
| 5,360,004 | A | 11/1994 | Purdy et al. | |
| 5,361,758 | A | 11/1994 | Hall et al. | |
| 5,460,177 | A | 10/1995 | Purdy et al. | |
| 5,529,755 | A | 6/1996 | Higashio et al. | |
| 5,703,364 | A | 12/1997 | Rosenthal | |
| 5,747,806 | A | 5/1998 | Khalil et al. | |
| 5,910,109 | A | 6/1999 | Peters et al. | |
| 6,043,492 | A | 3/2000 | Lee et al. | |
| 6,049,727 | A * | 4/2000 | Crothall | ............... 600/310 |
| 6,097,975 | A | 8/2000 | Petrovsky et al. | |
| 6,151,517 | A * | 11/2000 | Honigs et al. | ............... 600/322 |
| 6,425,865 | B1 * | 7/2002 | Salcudean et al. | ............... 600/437 |
| 6,438,147 | B1 | 8/2002 | Roychoudhuri et al. | |
| 2005/0043606 | A1 * | 2/2005 | Pewzner et al. | ............... 600/407 |

* cited by examiner

OTHER PUBLICATIONS

Mirov et al., Diode and fibre pumped Cr:ZnS mid-infrared external cavity and microchip lasers, IEE Proc.-Optoelectron, vol. 150, No. 4, Aug. 2003.*

*Primary Examiner*—Eric F. Winakur
(74) *Attorney, Agent, or Firm*—Dinsmore & Shohl LLP

(57) ABSTRACT

A system and method for determining the concentration of analytes of interest in complex matrices is provided. According to one aspect of the present invention, near-infrared analytical radiation is generally directed onto a portion of a specimen containing the analyte of interest. A wavelength of the analytical radiation is scanned over the specimen over a broad range of frequencies and over a short duration of diagnostic time. A spectrum of radiation is transmitted through, reflected from or scattered from the specimen and collected by a detector. The concentration of the analyte of interest in the specimen is determined by the radiation collected by the detector.

46 Claims, 1 Drawing Sheet

NON-INVASIVE DETECTION OF ANALYTES IN A COMPLEX MATRIX

CROSS-REFERENCE TO RELATED APPLICATIONS

This application claims the benefit of U.S. Provisional Application Ser. No. 60/436,761, filed Dec. 27, 2002.

BACKGROUND OF THE INVENTION

The present invention relates to the determination of the concentration of various analytes of interest in various complex matrices. The invention is applicable in a broad range of chemical analyses in a variety of fields including, but not limited to, non-invasive blood analysis and other medical applications, food and pharmaceutical industries, environmental monitoring, industrial safety, etc. In the analysis of blood, blood glucose concentration and measurements of cholesterol and tryglicerides concentrations in blood are of significant importance.

BRIEF SUMMARY OF THE INVENTION

In accordance with one embodiment of the present invention, a method and system for determining the concentration of analytes of interest in complex matrices, for example, glucose in blood, is provided. Analytical radiation is generated and directed onto a portion of a specimen containing the analytes of interest. The wavelength of the analytical radiation is scanned over a broad analytical spectral range and over a relatively short duration of diagnostic time. The analytical radiation attenuated by the specimen is collected. Subsequently, the amount of collected radiation attenuated by the specimen is correlated to the concentration of the analyte of interest in the specimen. The concentration of the analyte of interest in the specimen then may then be displayed on an output display device as well as used as input into an analyte control device, such as an insulin pump. Multivariate analysis techniques may be used to relate measured spectra to the concentration of the analyte of interest.

Other embodiments of the present invention may be utilized to overcome the problem of insufficient signal-to-noise ratio in measurements of glucose and other analytes of interest in the specimen. An increase in signal-to-noise ratio allows measurements to be taken within a relatively short duration of diagnostic time, which helps to eliminate problems associated with hardware and specimen noise.

It is an object of the present invention to meet the well perceived need for a simple and reliable method of measurements of analytes in complex matrices, as well as the need for a portable, rugged device for non-invasive measurements of blood constituents, in particular, blood glucose monitoring in diabetic subjects.

It is another object of the present invention to use the present invention in contexts where the rather weak absorptivity of some compounds, e.g., glucose, imposes challenging requirements on the signal-to-noise ratio in the spectra for analysis.

Other objects of the present invention will be apparent in light of the description of the invention embodied herein.

BRIEF DESCRIPTION OF THE SEVERAL VIEWS OF THE DRAWINGS

The following detailed description of specific embodiments of the present invention can be best understood when read in conjunction with the following drawing in which.

Figure 1:
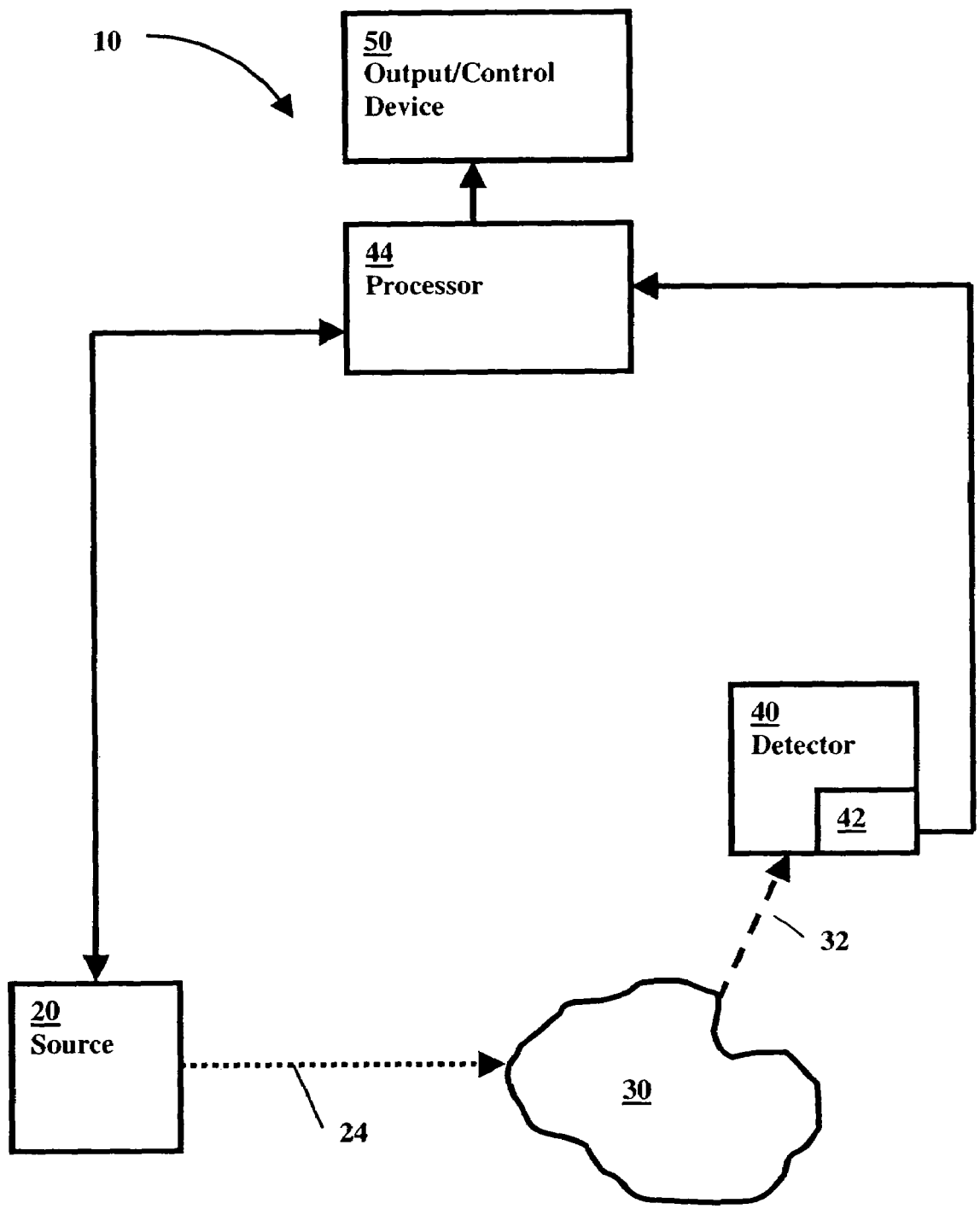
FIG. 1 is a schematic diagram of a system for detecting an analyte in a specimen according to an embodiment of the present invention.

In the following detailed description of the preferred embodiments, reference is made to the accompanying drawing that forms a part hereof, and in which is shown by way of illustration, and not by way of limitation, a specific embodiment in which the invention may be practiced. It is to be understood that other embodiments may be utilized and that logical, mechanical and electrical changes may be made without departing from the spirit and scope of the present invention.

DETAILED DESCRIPTION

Referring to FIG. 1, a system 10 for detecting an analyte in a specimen 30 according to an embodiment of the present invention is illustrated. It is contemplated that specimens according to the present invention may comprise biological or non-biological specimens. Biological specimens according to the present invention include, but are not limited to, specimens characterized by a cardiac cycle. A variety of non-biological specimens are contemplated by the present invention including, but not limited to, water, food, air, etc. Analytes of interest may include components ordinarily present in the specimen of interest, e.g., glucose in blood or tissue, or components that represent pollutants or contaminants in a specimen of interest.

The system 10 comprises a radiation source 20 and a detector 40. In one embodiment, both the radiation source 20 and the detector 40 are portable and rugged. The radiation source 20 may be, for example, a laser, an optical parametric oscillator (OPO), or a light emitting diode (LED). The radiation source 20 may be a single broadly tunable laser. Suitable lasers, include, but are not limited to, a semiconductor laser diode, a fiber laser, a solid state laser, a quantum cascade laser, or a color center laser. Semiconductor lasers are compact and power efficient and allow the system 10 to be more readily portable. Cr doped ZnSe, ZnS, or CdS lasers are also contemplated because of particular advantages in the context of wavelength scanning. In one embodiment, the radiation source 20 is an external cavity semiconductor laser diode. In addition, the radiation source 20 may employ the Littman-Metcalf, Littrow, or any other suitable external cavity configuration.

The radiation source 20 is configured to generate analytical radiation and scan over an analytical spectral range. The analyte of interest present within the specimen 30 has unique absorption spectrum within the analytical spectral range. For example, glucose in blood is characterized by an absorption spectrum that includes absorption lines at about 1.56 µm, 2.15 µm, 2.27 µm, and 2.32 µm, each within a source spectral range of between 900 nm and 2700 nm.

In one embodiment of the present invention, the radiation source 20 scans a wavelength of the analytical radiation over the analytical spectral range over a predetermined diagnostic time period. The duration of the diagnostic time period is relatively short. For example, in embodiments where the specimen is biological and is characterized by a cardiac cycle, the diagnostic time period is no greater than the duration of the cardiac period of the specimen. For example, a cardiac period of a human typically ranges from about 0.3 to about 2 seconds. Typically, the duration of the diagnostic time period is a fraction of the cardiac period (e.g., less than one half of the cardiac period). For example, the duration of the diagnostic time period may be 0.01 second in the case of determining blood glucose concentration in a human.

The analytical radiation emitted by the radiation source 20 may define a relatively narrow spectral line with a width of less than about 20 nm. Preferably, the spectral line width is about 1 nm. The analytical spectral range may from between about 900 nm and about 2700 nm and should be broad enough to discriminate the contributions of any other analytes present in the specimen 30. In the case of blood glucose, the range is broad enough to discriminate from the contributions of the other analytes in the human body, such as, for example, urea, proteins and other similar analytes. An analytical spectral range from about 2050 nm to about 2400 nm may be suitable in many contexts. The radiation source 20, in addition, may also be configured to control the width of the analytical spectral range.

The radiation source 20 delivers the analytical radiation to the specimen 30. The detector 40, in turn, collects the radiation reflected from, scattered from, or transmitted through the specimen 30 of the analytical radiation. Collection of radiation transmitted through the specimen 30 is most suitable for specimen areas that are relatively thin. For example, if the specimen 30 is human, the transmissions can be collected from the ear, the web area between the thumb and index finger, skin pinch on the back of the hand, or in any other similar thin area of the body where transmissions may be collected through the specimen 30. Radiation reflected or scattered from a nail of a finger or toe is another potential site of collection of the analytical radiation if the specimen 30 is human.

In another embodiment, the radiation source 20 may be configured to utilize optics to aid in directing the analytical radiation onto the specimen 30. In the same vein, the detector 40 may also be configured to utilize optics to aid in collections of the attenuated analytical radiation from the specimen 30.

In yet another embodiment, conduits are used to deliver the analytical radiation to the specimen 30 as well as to collect the reflected, scattered, or transmitted radiation from the specimen 30. A conduit 24 delivers the analytical radiation from the source 20 to the specimen 30. Another conduit 32 collects the reflected, scattered, or transmitted radiation from the specimen 30 to the detector 40.

The conduits 24, 32 may be, for example, a fiber optic bundle. Because the conduits 24, 32 need to be highly transparent for wavelengths as long as 2700 nm, the material used for the conduits 24, 32 can be for example, ultra-low OH silica, quartz, sapphire, ZBLAN glass, or any similar suitable material. ZBLAN is fluorine combined with the metals zirconium, barium, lanthanum, aluminum, and sodium (Zr, Ba, La, Al, and Na, hence its name). The use of the fiber optic bundle conduits 24, 32 has the advantage of allowing for relatively remote placement of the system 10. The conduits 24, 32 may also be air, the tissue of the specimen 30 itself, or any suitable transmission medium.

The detector 40 may be a single detector or a multi-channel detector array. The detector 40 may have a high sensitivity to the wavelength of analytical radiation used. The detector 40 may be, for example, PbS, HgCdTe, HgCdZnTe, InGaAsSb/AlGaAsSb, or any other suitable detector for the wavelength of analytical radiation used. For example, the detector 40 may be an extended InGaAs pin photodiode for detecting measurements in the analytical spectral ranges of between about 1000 nm and about 2600 nm. An alternative, more economical detector 40 is a silicon photodiode, which is particularly useful where the analytical spectral range is less than about 1000 nm. For increased sensitivity, the detector 40 may be cooled by using, for example, a cryogenic or thermoelectric cooler.

The radiation source 20 and the detector 40 are configured such that the intensity of the analytical radiation received by the detector 40 is subject to attenuation by the analyte within at least a portion of the analytical spectral range. This attenuation is recorded as a function of wavelength. The detector 40 is configured to receive the analytical radiation and generate a signal indicative of attenuation of the analytical radiation over at least a portion of the analytical spectral range. An analog-to-digital converter 42 may be provided to convert the signal indicative of attenuation of the analytical radiation into a digital signal.

The system 10 may also contain a processor 44. The processor 44 may be configured to receive the digital signal indicative of attenuation of the analytical radiation from the analog-to-digital converter 42. The processor 44 determines the absorption spectrum in the analytical spectral range wherein the analyte of interest has a distinct absorption spectrum. The processor 44 correlates the absorption spectrum of the analytical radiation with an analyte of interest in the specimen 30 to arrive at the concentration of the analyte of interest in the specimen 30.

The processor 44 then transfers the concentration value to an output/control device 50 or another device external to the system 10. The output/control device 50 may be an output display device which then displays the concentration of the analyte of interest. Alternatively, or additionally, the output/control device 50 may be an analyte control device that is configured to react in accordance to the inputted concentration of the analyte of interest by adjusting the levels of analyte of interest concentration in the specimen 30. The analyte control device can be, for example, an insulin pump when the analyte of interest is blood glucose, but any other similar control device can be used.

In one embodiment of the present invention, the processor 44 utilizes step scanning. With step scanning, the radiation source 20 is fixed at a single wavelength. The signals from the radiation source 20 are accumulated and averaged by the processor 44 until the desired signal-to-noise ratio is established. The signal-to-noise ratio may be established by calculation, measurement, input, or by any suitable means of establishing a signal-to-noise ratio. After the desired signal-to-noise ratio is established, the radiation source 20 moves to the next wavelength and the process is repeated until the desired signal-to-noise ratio is established at the next wavelength. This process continues over the target spectral range. For example, signals from ten distinct wavelengths between 2.1 µm and 2.4 µm may be accumulated and averaged by the processor 44.

In another embodiment, the radiation source 20 scans across the entire analytical spectral range over a very short time duration, usually within a fraction of the cardiac period if the specimen 30 is biological and characterized by a cardiac period. The processor 44, in turn, collects the measurements across the entire analytical spectral range and determines the signal-to-noise ratio. The process of scanning across the entire analytical spectral range over a very short time duration is repeated until the desired signal-to-noise ratio is achieved. By taking the measurements within a fraction of the cardiac period, this technique results in an essentially static testing environment, helping to eliminate hardware and specimen noise, thereby, resulting in increased signal quality.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A system for detecting an analyte in a specimen characterized by a given cardiac period; the system comprising:
   a radiation source configured to generate analytical radiation such that a wavelength of said analytical radiation scans an analytical spectral range over a diagnostic time period, wherein
      said analyte is characterized by an absorption spectrum within said analytical spectral range and
      a duration of said diagnostic time period is a fraction of said cardiac period;
   a detector configured to receive said analytical radiation and generate a signal indicative of attenuation of said analytical radiation over at least a portion of said spectral range, wherein said radiation source and said detector are configured such that an intensity of said analytical radiation received by said detector is subject to attenuation by said analyte within at least a portion of said analytical spectral range; and
   a processor configured to receive said attenuation signal until a desired signal-to-noise ratio associated with said attenuation signal is established by said processor.

2. The system of claim 1, wherein the duration of said cardiac period ranges from about 0.3 to about 2 seconds.

3. The system of claim 2, wherein the duration of said diagnostic time period is less than one half of said cardiac period.

4. The system of claim 2, wherein the duration of said diagnostic time period is less than about 5% of said cardiac period.

5. A system for detecting an analyte in a specimen; the system comprising:
   a radiation source configured to generate a single beam of analytical radiation and to scan a wavelength of said single beam of analytical radiation over an analytical spectral range, wherein said analyte is characterized by an absorption spectrum within said analytical spectral range; and
   a detector configured to receive said single beam of analytical radiation and from said received single beam of analytical radiation generate a signal indicative of attenuation of said single beam of analytical radiation over at least a portion of said spectral range, wherein said source and said detector are configured such that an intensity of said analytical radiation received by said detector is subject to attenuation by said analyte within at least a portion of said analytical spectral range; and
   a processor configured to receive said attenuation signal until a desired signal-to-noise ratio associated with said attenuation signal is established by said processor.

6. The system of claim 5, wherein said analytical spectral range lies between about 900 nm and about 2700 nm.

7. A system for detecting an analyte-of-interest in a specimen; the system comprising a radiation source, a detector, and a processor, wherein:
   said radiation source is configured to
      generate analytical radiation characterized by a spectral line width less than about 20 nm over an analytical spectral range from about 900 nm to about 2700 nm,
      control the spectral width of said analytical spectral range so as to enable discrimination between said analyte-of-interest and other analytes in said specimen,
      scan a wavelength of said analytical radiation over said controlled spectral width;
   said detector is configured to receive said analytical radiation and generate a signal indicative of attenuation of said analytical radiation over at least a portion of said spectral range;
   said source and said detector are configured such that an intensity of said analytical radiation received by said detector is subject to attenuation by said analyte within at least a portion of said analytical spectral range; and
   said processor is configured to receive said attenuation signal until a desired signal-to-noise ratio associated with said attenuation signal is established by said processor.

8. The system of claim 7, wherein said radiation source comprises one of a laser, a light emitting diode, an optical parametric oscillator, and combinations thereof.

9. The system of claim 7, wherein said radiation source comprises one of a semiconductor laser diode, a color center laser, a fiber laser, a solid state laser, a quantum cascade laser and combinations thereof.

10. The system of claim 7, wherein said radiation source comprises a single tunable laser.

11. The system of claim 7, wherein said radiation source comprises an external cavity laser.

12. The system of claim 11, wherein said external cavity laser comprises one of a Cr doped ZnSe, ZnS and CdS laser.

13. The system of claim 11, wherein said external cavity laser defines a Littman-Metcalf configuration.

14. The system of claim 11, wherein said external cavity laser defines a Littrow configuration.

15. The system of claim 7, wherein said analyte is characterized by a given cardiac period of said specimen.

16. The system of claim 15, wherein said radiation source is further configured to generate said analytical radiation over a diagnostic time period.

17. The system of claim 16, wherein said diagnostic time period is no greater than a duration of said cardiac period.

18. The system of claim 17, wherein the duration of said cardiac period ranges from about 0.3 to about 2 seconds.

19. The system of claim 17, wherein the duration of said diagnostic time period is less than one half of said cardiac period.

20. The system of claim 16, wherein the duration of said diagnostic time period is less than about 5% of said cardiac period.

21. The system of claim 7, wherein said analytical radiation is characterized by a spectral line width of about 1 nm.

22. The system of claim 7, wherein a width of said analytical spectral range is between about 50 nm and 400 nm.

23. The system of claim 7, wherein said analytical spectral range lies between about 2050 nm and about 2400 nm.

24. The system of claim 7, wherein said detector is configured to receive analytical radiation reflected from said specimen.

25. The system of claim 7, wherein said detector is configured to receive analytical radiation scattered from said specimen.

26. The system of claim 7, wherein said detector is configured to receive analytical radiation transmitted through said specimen.

27. The system of claim 7, further comprising:
an analog-to-digital converter configured to convert said signal indicative of attenuation of said analytical radiation into a digital signal.

28. The system of claim 7, wherein the radiation source and the detector are portable.

29. The system of claim 7, further comprising:
a processor configured to receive said signal indicative of attenuation of said analytical radiation from said detector.

30. The system of claim 29, wherein the processor is further configured to determine an absorption spectrum over the analytical spectral range.

31. The system of claim 30, wherein the processor is further configured to correlate the absorption spectrum with an analyte of interest in said specimen.

32. The system of claim 31, wherein the processor is further configured to determine a concentration of said analyte of interest.

33. The system of claim 32, further comprising:
an analyte control device to receive said concentration of said analyte of interest as input.

34. The system of claim 33, wherein the analyte control device is
configured to adjust levels of analyte of interest concentration in said specimen as function of the inputted concentration of said analyte of interest.

35. The system of claim 33, wherein the analyte control device comprises an insulin pump.

36. The system of claim 7, wherein said radiation source is configured to maintain said radiation source fixed at a single wavelength until said signal-to-noise ratio exceeds a given value.

37. The system of claim 36, wherein said radiation source is configured to step to another wavelength in said analytical spectral range after achieving said desired signal-to-noise ratio.

38. The system of claim 7, wherein said radiation source is configured to repeat said scan over said analytical spectral range until said signal-to-noise ratio exceeds a given value.

39. The system of claim 7, wherein the analyte comprises one of glucose, urea, cholesterol, ketone, creatinine, bilirubin and proteins.

40. The system of claim 7, wherein the analyte comprises one of a contaminant and a pollutant.

41. The system of claim 7, wherein said specimen is a biological specimen.

42. The system of claim 41, wherein said analytical radiation received by said detector is reflected or scattered from said biological specimen over at least a portion of said spectral range.

43. The system of claim 41, wherein said analyte-of-interest in said biological specimen is in the proximity of a nail plate of a digit of said biological specimen.

44. The system of claim 7, wherein said processor establishes said desired signal-to-noise ratio by fixing said analytical radiation at a single wavelength, accumulating and averaging signals at said single wavelength until reaching said desired signal-to-noise ratio, stepping to a next wavelength, accumulating and averaging signals at said next wavelength until reaching said desired signal-to-noise ratio, repeating stepping, accumulating and averaging over all wavelengths of said spectral range within a fraction of a cardiac period of said specimen.

45. The system of claim 7, wherein said radiation source repeats said scan over said analytical spectral range within a fraction of a predetermined diagnostic time period until said signal-to-noise ratio exceeds a given value.

46. The system of claim 7, wherein said radiation source scans a single wavelength within a fraction of a predetermined diagnostic time period until said signal-to-noise ratio exceeds a given value and steps to another wavelength in said analytical spectral range after said signal-to-noise ratio is established.

* * * * *